(12) United States Patent
Brunk et al.

(10) Patent No.: US 6,711,936 B2
(45) Date of Patent: Mar. 30, 2004

(54) SOCK TESTING METHOD AND APPARATUS FOR PERFORMING THE SAME

(75) Inventors: Donald H. Brunk, Boothwyn, PA (US); Jill A. Conley, Chesterfield, VA (US); Douglas K. Farmer, Greensboro, NC (US); Tony M. Whitener, Taylorsville, NC (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/213,195

(22) Filed: Aug. 5, 2002

(65) Prior Publication Data
US 2004/0020263 A1 Feb. 5, 2004

(51) Int. Cl.[7] .......................... G01N 19/02; G01N 3/56
(52) U.S. Cl. .................. 73/9; 73/9; 73/159; 73/579
(58) Field of Search .................. 73/9, 159, 579

(56) References Cited

U.S. PATENT DOCUMENTS

| | | | | |
|---|---|---|---|---|
| 3,442,120 A | * | 5/1969 | Russenberger et al. ....... | 73/805 |
| 3,975,956 A | * | 8/1976 | Peel ........................... | 73/159 |
| 4,137,763 A | * | 2/1979 | Swallow ...................... | 73/159 |
| 4,561,267 A | | 12/1985 | Wilkinson et al. | |
| 5,491,306 A | | 2/1996 | Gram | |
| 5,945,607 A | | 8/1999 | Peppel et al. | |
| 6,357,100 B2 | | 3/2002 | Speller, Jr. et al. | |
| 6,362,557 B1 | | 3/2002 | Gruber et al. | |
| 6,523,729 B1 | * | 2/2003 | Gardon-Mollard .......... | 223/112 |

* cited by examiner

Primary Examiner—Hezron Williams
Assistant Examiner—Andfe K. Jackson
(74) Attorney, Agent, or Firm—Robert B. Furr, Jr.

(57) ABSTRACT

The present invention generally relates to both an apparatus, a test form and a method for evaluating sock-drop. More particularly, the present invention relates to an apparatus able to simulate particular forces exerted by human movements, a test form resembling a human leg as well as a method for testing sock-drop so that properties such as compression and comfort can be balanced.

6 Claims, 4 Drawing Sheets

SOCK TESTING METHOD AND APPARATUS FOR PERFORMING THE SAME

BACKGROUND OF THE INVENTION

The present invention relates to an apparatus and a test form utilized to test sock-drop over a period of time, as well as a method of determining sock-drop.

As is generally known, socks have a tendency to sag and bulk over the course of the day due to agitation and/or gravitational forces and/or impact forces resulting from the gait or other movements of a person. In order to prevent sock-drop, people have used devices, such as, for example, sock garters to prevent socks from sagging and thereby causing an unkempt, disheveled or tousled appearance. These restraints attached to the top of the user's sock via clips and utilized an elastic band located between the user's knee and calf muscle as the support base. Subsequently, elastic threads were developed, which allowed the sock garters to be discarded because the socks were capable of remaining aloft independently. Various types of elastic yarns are available as sock components, each having a particular level of performance. For example, polyester or nylon fiber can be given a mechanical crimp (texturing process) which provides some level of stretch and recovery to the sock fabric, however, the mechanical crimp can fade over time due to washing and wearing. Thus, as the sock ages, its ability to hold its shape and remain at the desired place on a human leg diminishes. In addition, due to walking and/or similar movements, all socks would sag and eventually buckle or slide down the wearer's leg in response to the downward forces acting on the sock. To combat sock-drop, socks were constructed such that the elastic incorporated therein would exert sufficient levels of pressure against a wearer's leg, however, this often caused discomfort, such as skin irritation or indentation, when the socks were worn for any length of time.

Within the industry, consumers consistently register complaints in regards to two specific issues, (1) discomfort due to sock tightness, and (2) sock-drop. Typically, these aspects are considered to be mutually exclusive of one another, such that, in order to counteract sock-drop the tightness of the sock against the leg must be increased to a sufficient level. Conversely, in order to maximize comfort, sock tightness must be reduced, which reintroduces sock-drop. Therefore, the present invention solves a long-felt need within the industry because both the method of testing and the testing apparatus allow manufacturers to optimize the level of tightness to minimize the sock-drop and maximize comfort, thereby allowing manufacturers to properly address consumer complaints.

Typically, sock-drop testing is carried out using human beings to assess the capabilities of a particular sock, wherein participants either move about and report the amount of sock-drop resulting from their movements or a technician observes the amount sock-drop after a specified period of time. However, such methods are time consuming and make it difficult to reproduce reliable data due to human variability. These methods allow for too many external factors to interfere with and impact upon the performance of the sock, such as the forces exerted on the sock by a pant leg, leg flexion or muscle contractions.

Instruments are available for testing socks, however such units are designed to only test stretch/compression levels (i.e., U.S. Pat. No. 3,975,956 to Peel), or the amount of force exerted upon the wearer's leg by the sock. These instruments do not have the capability of simulating the momentum forces associated with the human gait or walking movements in order to evaluate sock-drop. Therefore, there is no apparatus or test method currently available and it has been necessary to adapt an existing apparatus for use in the present invention and develop a test method. Thus, there is a need within the industry to develop a method for testing socks in order to ascertain the necessary components, and amounts of each, to allow for optimal balancing of fabric compression, comfort and avoidance of sock-drop.

An object of the present invention is to provide an apparatus capable of assessing the effects of human walking movements on sock-drop, as well as a method of testing sock-drop that is rapid and objective.

SUMMARY OF THE INVENTION

The present invention relates to a sock testing apparatus comprising:
  a) a means for agitation; and
  b) a test form removably attached to said means for agitation.

The present invention further contemplates a method for testing sock-drop. More specifically, the present invention relates to a method comprising the steps of:
  (a) loading a sock onto the test form, wherein the sock is positioned on the test form having a wear dimension;
  (b) agitating the test form having the sock thereon with a reciprocating motion, for a predetermined time, along the main axis;
  (c) measuring a sock-drop distance traveled by the sock; and optionally
  (d) observing whether buckling of the sock occurred; and
  (e) recording the elapsed time from the start of the test until bucking occurred,
  where steps (d) and (e) are optional and may be taken by one skilled in the art if sock buckling and the time until such buckling occurred are desired data.

DETAILED DESCRIPTION

Figure 1:
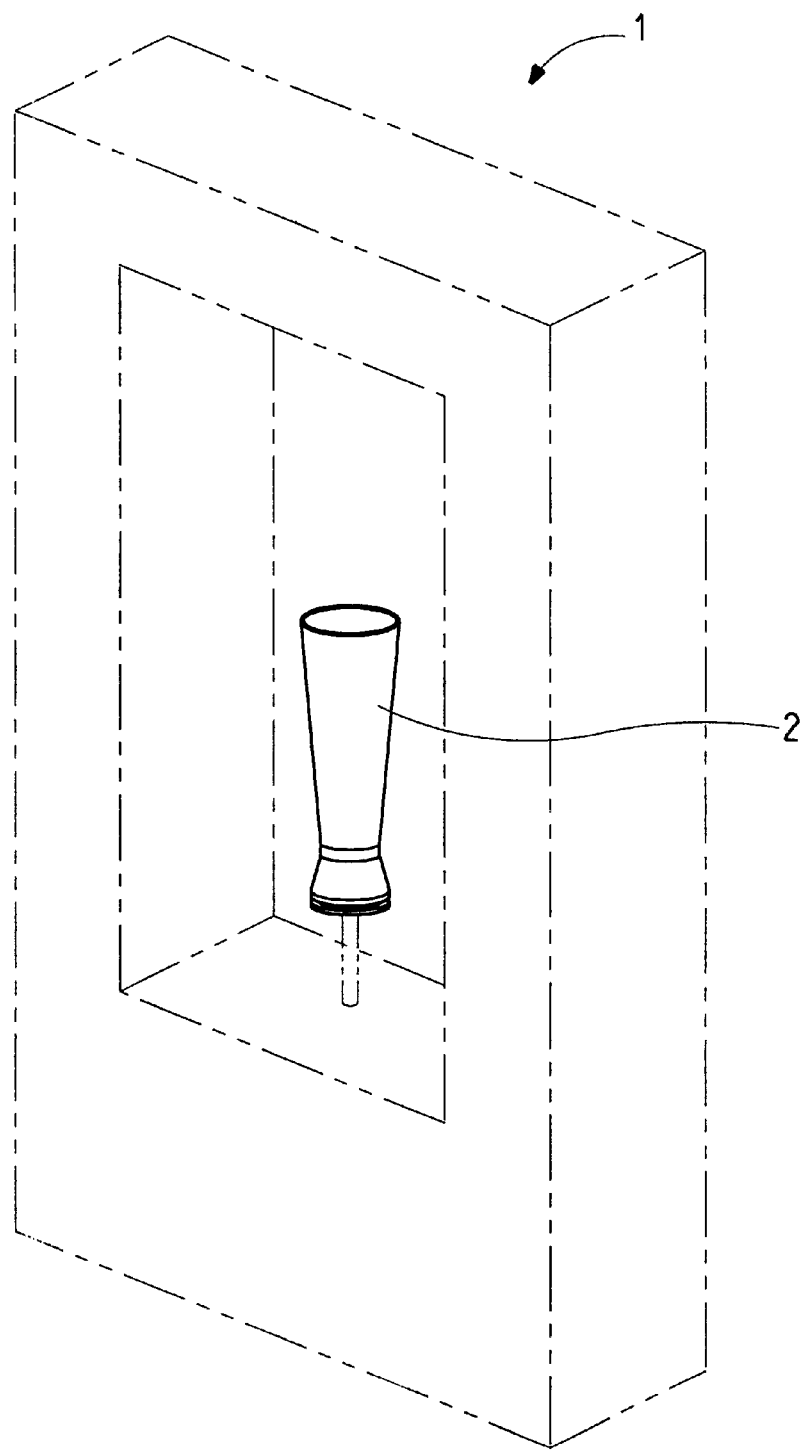
FIG. 1 depicts a perspective view of the test form removably attached on the means for agitation.

The present invention provides several advantages, including, (1) an apparatus and method to test sock-drop, which yield objective results, rather than subjective results based on human observations and variable human characteristics, (2) an apparatus and method which allow for the faster turnaround of experiments, and thus, the rapid acquisition of data, (3) an apparatus and method that are more economical in procuring sock-drop data than other systems currently used within the industry, and (4) an apparatus and method to predict the propensity of a sock to buckle. The method according to the present invention provides data regarding the initial and final positioning of the sock top, whether buckling of the sock occurred, the length of time from the start of the test until buckling began, and initial stretch recovery. This data is more reliable than data obtained via other currently known means due to a minimizing of external variables and an absence of human interference.

As used herein, the term "buckling" shall refer to a circumstance where a test sock has exhibited sag as a result of the method of the present invention, such that large folds are present in the sock, generally found at, or around, the ankle. Buckling is generally associated with a severe degree of sock-drop.

As used herein, the term "wear dimension" shall refer to the orientation or positioning of a test sock on the test form in substantially the same manner as it would be positioned on a human leg form, such that the sock is subjected to substantially the same stresses and forces as a sock worn on a human leg.

As used herein, the term "main axis" shall refer to the axis that runs the length of the test form and is utilized to describe the directional motion of the test form during agitation.

As used herein, the term "plating yarn" shall refer to a yarn that is used in knitted fabric, wherein the fabric is knitted from two yarns of different properties, such that one yarn is on the face of the fabric, the other on the back of the fabric. Plating yarn is the component of a sock that provides the stretch and recovery property. For example, a cotton sock is predominantly constructed of cotton (to provide softness, wicking, and warmth), however the sock also includes the plating yarn giving it the ability to stretch. The particular type of plating yarn utilized in the sock can affect the properties of the sock such as, for example, the rate of sock-drop, the amount of total sock-drop, and the time until buckling.

As used herein, the term "sock-drop" shall refer to the distance traveled by the sock top during agitation. More particularly, prior to agitation at least one specific orientation marker on the sock, namely an initial position, is determined and subsequent to agitation the final position of that marker is determined, wherein the distance between the initial and final positions is measured and known as the sock-drop distance.

In addition to the character of the sock and its components and independent of the momentum forces, there are several external factors or parameters that will affect the sock-drop, such as, for example, the shape of the test form, the frictional properties of the surface of the test form and the peak deceleration of the movement of the form. However, such external factors can be controlled in order to provide results that exclude variations caused by human interference, such that a determination of the sock components can be made in order to optimize the balancing of compression, comfort and avoidance of sock-drop.

The present invention relates to a sock testing apparatus comprising:

a) a means for agitation; and b) a test form removably attached to said means for agitation.

A critical aspect of the present invention is that the apparatus utilizes, in magnified form, one of the primary downward forces that act upon a sock (3) during walking. More particularly, the present invention utilizes the momentum forces of the sock fabric created by the downward deceleration of the wearer's leg and foot when the heel impacts a floor.

A means for agitation (1) for creating these momentum forces may be any conventional device generally known within the art capable of producing motions of sufficient magnitude and speed to agitate the test form, preferably producing a reciprocating motion including, but not limited to, for example, high rate testing systems (such as the Model 819 and others produced by MTS Systems Corporation (Eden Prairie, Minn.)), shaker tables, pneumatic devices and hydraulic devices. While it is anticipated that simpler, more economical versions of the apparatus could be built using cams, cranks, or other mechanisms to provide a reciprocating motion which are all well known to those skilled in the art, a preferred embodiment of the present invention utilizes a sophisticated computer-controlled high speed servohydraulic actuating system, such as for example a Model 819 High Rate Testing System, manufactured by MTS Systems Corporation (Eden Prairie, Minn.). Further description of the means for agitation for the present invention is disclosed by U.S. Pat. Nos. 3,442,120; 3,800,588; 3,908,429; 4,274,290; 4,290,343; 4,336,745; 4,457,684; 4,457,072; 4,458,189; 4,470,787; 4,478,086; 4,501,139; 4,531,901; 4,537,077; 4,679,591; 4,794,540; 4,802,367; 4,952,873; 4,958,332; 5,661,446; 5,491,306; 5,945,607; 5,959,374, which are all hereby incorporated by reference in their entireties.

Another aspect of the present invention is the magnitude of the deceleration which produces the inertial forces in the sock, which in the present invention the peak deceleration is up to 60 times the force of gravity, preferably in the range from about 30 to 60 times the force of gravity and more preferably about forty times greater than the force of gravity (also known as 40 G's). Higher G forces may be utilized in assessing lighter weight socks, such as flat knit socks.

Generally, the present invention magnifies those momentum forces associated with the human gait. More particularly, the present invention has the motion profile depicted in Table 1 as given to the computer of the preferred embodiment, although this motion profile may be duplicated by one skilled in the art using conventional devices capable of producing a reciprocating motion. However, the actual motion profile is not as sharp as that shown in Table 1 since the preferred means for agitation of the present invention does not generally respond instantly to a change in direction and therefore requires some finite amount of time to reverse the direction and speed. Table 2 shows the time and corresponding displacement value for three cycles of the preferred embodiment of the present invention.

TABLE 1

MOTION PROFILE

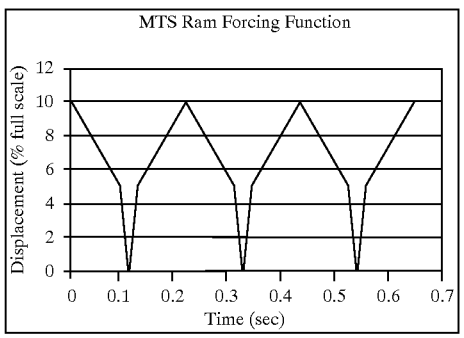

TABLE 2

TIME AND DISPLACEMENT FOR PREFERRED EMBODIMENT

| Time | Displacement |
| --- | --- |
| 0 | 10 |
| 0.1 | 5 |
| 0.11 | 0 |
| 0.12 | 5 |
| 0.22 | 10 |
| 0.32 | 5 |
| 0.33 | 0 |
| 0.34 | 5 |
| 0.44 | 10 |
| 0.54 | 5 |
| 0.55 | 0 |
| 0.56 | 5 |
| 0.66 | 10 |

Applicants believe that the present invention approximates the motion profile associated with human walking movements and the impact of a person's heel on the floor, however the forces and deceleration of the present invention are magnified in the present invention. Many types of reciprocating motion can be applied to the test form to produce these momentum forces of the sock fabric created by the downward deceleration of the wearer's leg and foot when the heel impacts a floor, however it is important to note that every cycle of the reciprocation should be substantially the same so that the test and the momentum forces are repeatable, such as, for example sinusoidal motion, square wave motion or sawtooth motion. Preferably however, the present invention utilizes a reciprocating motion having different decelerations at a first end of the motion versus a second end of the motion because it allows the sock to experience the maximal inertial force in the direction towards the foot. This type of motion has the advantage of providing a higher inertial force in one direction than another. If the higher inertial force is employed in the direction towards the ankle, the test can be accelerated. Furthermore, this type of motion more closely mimics the actual wearing conditions during walking, where the greatest decelerations result from the impact of the heel striking the ground.

In the case of a sinusoidal motion, sawtooth motion or square wave motion the greatest decelerations occur at both ends of the motion and therefore the inertial forces acting upon the sock remain the same in magnitude but alternate in direction, thereby alternately pushing the sock towards the ankle and towards the calf. These types of motion do provide a high degree of deceleration, so long as the correct frequency and amplitude are used. All of these types of motion could be utilized to result in the desired effect of the present invention as long as the shape of the test form encourages the sock to migrate in the direction of the ankle.

Figure 3:
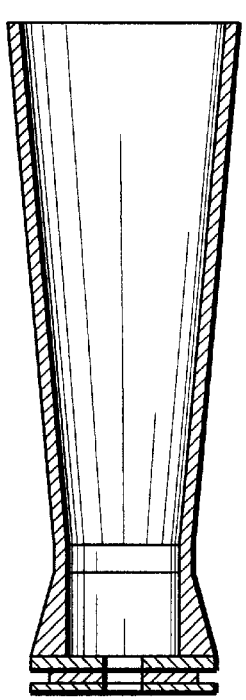
FIG. 3 depicts a side view of the test form, wherein the test form is hollow.
Figure 2:
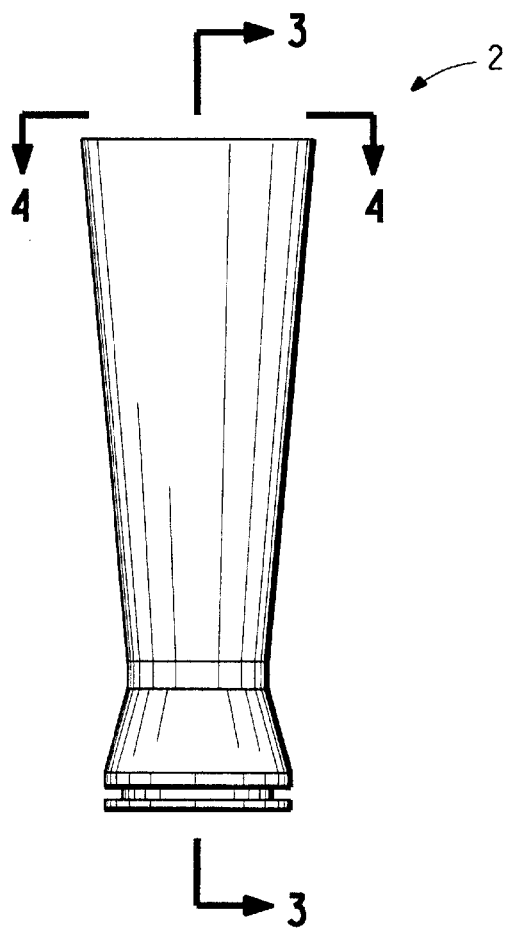
FIG. 2 depicts a side view of the test form, wherein the test form is a solid structure.
Figure 4:
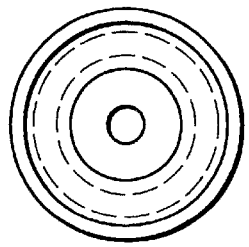
FIG. 4 depicts a cross-sectional top view of the test form of the present invention.
Figure 5:
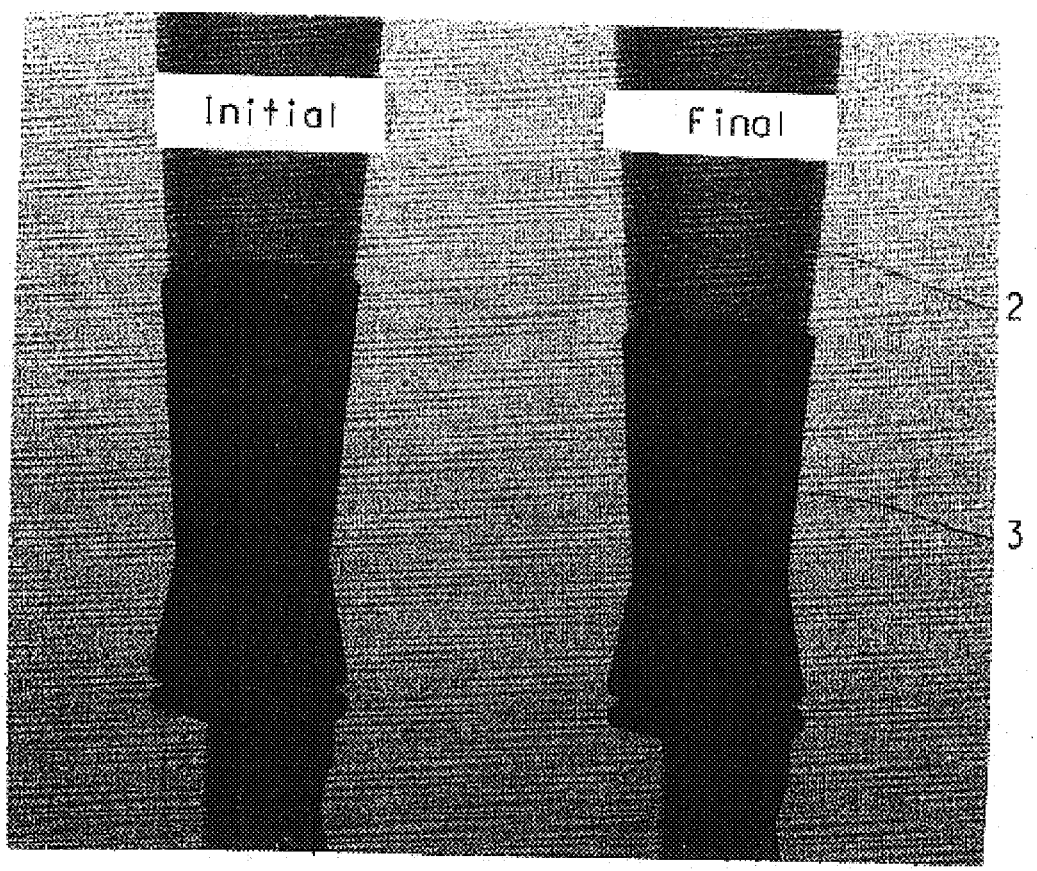
FIG. 5 depicts a side view of a test form according to the present invention having a sock thereon, wherein this Figure shows the sock at its initial position prior to agitation as well as the sock at its final position subsequent to agitation.
Figure 6:
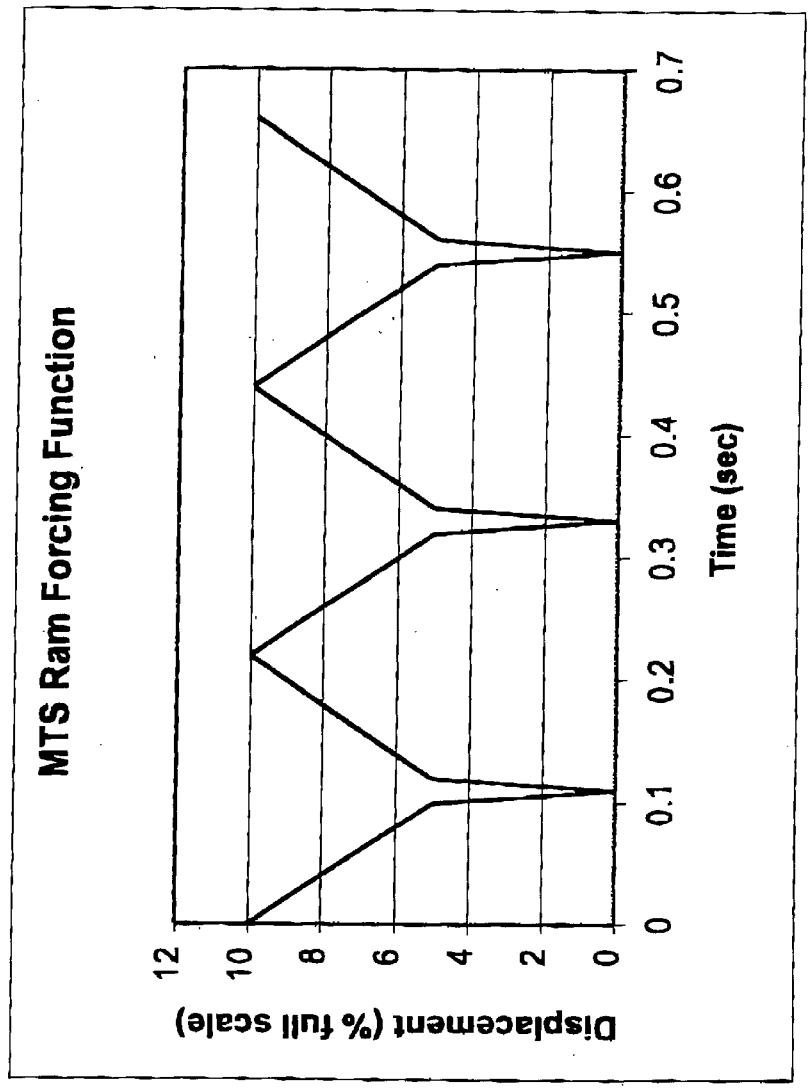
FIG. 6 depicts Table 1 showing an MTS Ram Forcing Function Motion Profile.

The present invention further contemplates and utilizes a test form (2) that is removably attached to a device which provides a controlled reciprocating motion, where the test form approximates the size, thickness and proportions of a human leg from a first position at the top of the foot to a second position on the calf just below the knee, wherein the circumferences of the test form at the first and second positions are substantially similar to those found on an average human (see FIGS. 1–5). The circumference and proportions of the test form may be adjusted and modified to accommodate any type of hosiery known within the art.

When a sock is loaded onto the test form and the form is caused to reciprocate vigorously, the top of the sock tends to move towards the ankle region of the form. The test form generally approximates the corresponding portions of a human leg rather than simply having a cylindrical shape. The test form preferably has a conical shape from the ankle region to the calf region. This conical shape assists the movement of the sock towards the smaller diameter region of the ankle and provides resistance to movement of the sock towards the larger diameter region of the calf. Typically, the test form has a groove machined into it at the foot end of the test form (below the ankle portion) such that an elastic band may be used to press the sock into the groove, which aids in positioning the sock on the test form. The test form may vary in its dimensions and typically resembles a human leg, however, preferably, the diameter at the location of the test form corresponding to an ankle is about 2.8 inches, the diameter at the location of the test form corresponding to the mid-calf level is about 4.6 inches, the distance from the ankle location to the mid-calf location is about 8.4 inches.

The removably attached test form and the means for agitation may have a variety of orientations, wherein it may be in a vertical position, horizontal position or at a position between the two, so long as the reciprocating motion is along the main axis of the test form, however a vertical orientation is preferred. If the form is oriented vertically with the calf region above the ankle region, gravity will also assist in moving the sock towards the ankle.

For ease of fabrication and attachment to the means of agitation, the test form was made without a foot portion and mounted at the end nearest the foot. However, a test form incorporating a foot shape and mounted at the end nearest the knee would provide additional ease of use when mounting and removing the sock being tested, and is contemplated by the present invention.

The test form may be constructed of any material capable of withstanding the forces exerted upon it by both the sock and the means for agitation, however it is preferably constructed of a light material such as aluminum or plastic. Moreover, the test form may be hollow, wherein the resulting reduction in weight makes it easier to agitate.

Additionally, the surface of the test form should have a level of friction high enough to initially overcome the downward forces acting upon a sock prior to agitation so that the sock can remain in its initial position until the method of the present invention has been activated. The coefficient of friction for the test form surface should be low enough to avoid impeding the tendency of the socks to drop upon sufficient agitation, such that socks of different stay-up characteristics cannot be distinguished from each other. Preferably, the coefficient of friction between the sock material and the test form surface is up to 0.5, and preferably below that of an average wearer's skin surface, which has been reported as being in the range of 0.3 to 0.5 for a variety of knitted fabrics. The lower coefficient of friction compensates for the absence of other forces that may tend to act upon the sock such as the interaction with the pants, the movement of the underlying muscles, and the stretching of the skin. It also accelerates the test so that it can be completed in a relatively short period of time.

While the present invention preferably utilizes the test form resembling a human's lower leg portion (i.e., the portion extending from the ankle to just below the knee) for the testing of socks, this invention may also be adjusted to test other types of hosiery, such as, for example, over-the-calf socks, knee socks and those types of hosiery that extend up to the middle or the upper thigh by developing a test form that simulates those portions of the human form. A skilled artisan will recognize and understand the necessary modifications that are required to be made to the test form described herein to result in a test form to accommodate the various types of hosiery described above.

The present invention further contemplates a method for testing sock-drop. More specifically, the present invention relates to a method comprising the steps of:
a) loading a sock onto a test form, wherein the sock is positioned on the test form having a wear dimension;
b) agitating the test form having the sock thereon with a reciprocating motion, for a predetermined time, along the main axis;
c) measuring a sock-drop distance traveled by the sock; and optionally
d) observing whether buckling of the sock occurred; and
e) recording the elapsed time from the start of the test until bucking occurred,
where steps (d) and (e) are optional and may be taken by one skilled in the art if sock buckling and the time until such buckling occurred are desired data.

The testing method according to the present invention generally included placing a sock onto a hosiery form and marking the location of the minimum circumference. The sock was then removed and loaded onto the test form, aligning the locatrion of the minimum circumference to a corresponding location on the test form. The sock was secured to the test form using an elastic band which pressed the sock into a groove machined into the foot end of the form for that purpose and the heel of the sock was slit open to accommodate attachment of the test form to the means of agitation, and the test form was subsequently attached to the means of agitation. The distance from the ankle to the top of the sock was measured and recorded. Agitation was initiated and continued for a predetermined period of time, generally between 1 and 3 minutes, however 2 minutes is preferred. Subsequent to agitation, the sock-drop was measured, any observed buckling of the sock was noted, and the time until buckling was recorded.

The loading of the sock onto the test form may be performed either manually or mechanically, however it is preferably manually loaded, wherein it has substantially the same wear dimension as a sock put on the leg and/or foot of the wearer. Thus, the fabric portion of the sock typically found over the ankle and lower leg of a wearer is similarly positioned on the test form of the present invention.

The embodiments of the present invention are further illustrated in the following Examples. It should be understood that these Examples, while indicating preferred embodiments and the most preferred embodiments of the present invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions. Thus various modifications of the present invention in addition to those shown and described herein will be apparent to those skilled in the art from the foregoing description. Although the invention has been described with reference to materials and embodiments, it is to be understood that the invention is not limited to the particulars disclosed, and extends to all equivalents within the scope of the claims.

EXAMPLES

The examples recited below particularly address socks that when worn, have their top portion at approximately mid-calf level although over-the-calf socks were also tested, however, it should be noted that with only small modifications, the apparatus and method of the present invention can accommodate any type of hosiery. Additionally, the measurements set forth below are provided in inches unless otherwise noted.

Various types of socks were tested utilizing the present invention. More specifically, the socks utilized in the sock stay-up examples were Men's 1×1 Gold Cup Socks, sizes 10–13, having a 1×1 top with a flatknit boot and foot. The socks were manufactured using an 84 needle double cylinder knitting machine. The Greige cross stretch was set to the same finished cross stretch for each sock construction, wherein the top was set to 8.75 inches and the foot was set to 8.5 inches. The Nylon control sock utilized in the Examples comprised 81% of 1/12 high bulk acrylic yarn and 19% of 2/70/34 type 6.6 nylon. The 20–146C sock comprised 79% of 1/12 high bulk acrylic yarn and 21% of 20 denier type 146C Lycra® air covered with 2/70/34 nylon. The 18–178C sock comprised 79% of 1/12 high bulk acrylic yarn and 21% of 18 denier type 178C Lycra® air covered with 2/70/34 nylon. The 25–178C sock comprised 79% of 1/12 high bulk acrylic yarn and 21% of 25 denier type 178C Lycra®) air covered with 2/70/34 nylon. The 35–178C sock comprised 79% of 1/12 high bulk acrylic yarn and 21% of 35 denier type 178C Lycra® air covered with 2/70/34 nylon. The ALC sock comprised 1/22 high bulk acrylic yarn where two ends of the yam were in the top of the sock and one end of the yarn was in the boot, and 20 denier type 162B Lycra® air covered with 2/70/34 nylon. The ANC sock comprised 1/22 high bulk acrylic yarn where two ends of the yarn were in the top of the sock and one end of the yarn was in the boot, and 2/70/34 nylon. The TUBE sock comprised 12/1 ring spun cotton and 2/70/34 nylon. In the AOTC sock, the sock top comprised 16/1 ring spun cotton, where two ends of the yarn were in the top of the sock and 60 denier D-06B Lycra® air covered with 1/70/34 nylon; whereas in the boot or foot the sock comprised 1 end of 12/1 ring spun cotton and 60 denier D-06B Lycra® air covered with 1/70/34 nylon. The DLLOTC sock comprised 16/1 TIMA cotton and 18 denier type 178C Lycra® air covered with 2/70/34 nylon, where the sock had graduated compression in the leg and laid in yarn (double covered Lycra® laid in throughout the leg for extra compression). The DNOTC sock comprised 16/1 TIMA cotton and 2/70/34 nylon, wherein this sock was an over-the-calf sock having a straight leg with no compression. The DLKOTC sock comprised 16/1 TIMA cotton and 60 denier D-06B Lycra® air covered with 2/70/34 nylon, wherein this sock had graduated compression in the leg and had laid in yarn only in the sock top and not throughout the leg (increase Lycra® denier in the plating yarn).

The socks tested according to the present invention were first placed onto a commercial hosiery form (RPM Industries, model number HM034-0) and the location of the minimum diameter just above the ankle was marked on the sock. The sock was then removed and mounted onto the test form which had been covered in Teflon® tape (manufactured by E. I. du Pont de Nemours and Company, Wilmington, Del.), such that the marked location was positioned at the center of the minimum diameter section of the test form. The sock was secured to the test form using an elastic band which pressed the sock into a groove machined into the foot end of the form for that purpose. The heel of the sock was slit open to accommodate attachment of the form to the means of agitation, and the test form was subsequently attached to the means of agitation which was a servohydraulic system from MTS (Model 819 High Rate Testing System), which employed the motion profile according to Tables 1 and 2 of this specification, such that the peak deceleration was forty times greater than the force of gravity. The distance from the ankle to the top of the sock (Height Above Ankle) was measured and recorded. The agitation was initiated and allowed to continue for two minutes. The distance from the ankle to the top of the sock was again measured, and any observed buckling of the sock was noted.

More particularly, the "Height Above Ankle" refers to the measured distance from the ankle to the top of the sock both at its initial position prior to agitation and at its final position subsequent to agitation. This value was calculated by measuring the distance from the top of the test form to the top of the sock and subtracting that distance from 11.6 (the measurement from the ankle to the top of the test form). Thus, the difference between the initial and final measurements constituted the sock-drop.

Example 1

Example 1 set forth the results from a first run, a second run and the average of these two runs of the present invention measuring the sock drop of mid-calf level socks. The results indicate the height of the sock top above the ankle portion of the test form at both its initial and final positions, wherein the sock-drop is the difference between these values.

TABLE 3

SOCK-DROP TEST - FIRST RUN

Height Above Ankle

| Sock Type | Initial | Final | Sock-Drop |
|---|---|---|---|
| 20-146C | 5.16 | 4.60 | 0.56 |
| 18-178C | 6.22 | 5.04 | 1.18 |
| 25-178C | 5.85 | 4.79 | 1.06 |
| 35-178C | 5.91 | 4.66 | 1.25 |
| 10 Den | 6.73 | 5.10 | 1.63 |
| Nylon | 8.10 | 5.60 | 2.50 |

TABLE 4

SOCK-DROP TEST - SECOND RUN

Height Above Ankle

| Sock Type | Initial | Final | Sock-Drop |
|---|---|---|---|
| 20-146C | 5.85 | 4.85 | 1.00 |
| 18-178C | 6.48 | 5.23 | 1.25 |
| 25-178C | 6.29 | 4.98 | 1.31 |
| 35-178C | 6.04 | 4.73 | 1.31 |
| 10 Den | 6.79 | 5.29 | 1.50 |
| Nylon | 8.48 | 4.60 | 3.88 |

TABLE 5

AVERAGED RESULTS FROM THE FIRST AND SECOND RUNS

Height Above Ankle

| Sock Type | Initial | Final | Sock-Drop |
|---|---|---|---|
| 20-146C | 5.51 | 4.73 | 0.78 |
| 18-178C | 6.35 | 5.13 | 1.22 |
| 25-178C | 6.07 | 4.88 | 1.19 |
| 35-178C | 5.98 | 4.69 | 1.29 |
| 10 Den | 6.76 | 5.19 | 1.57 |
| Nylon | 8.29 | 5.10 | 3.19 |

Example 2

Example 2 sets forth the results of agitating white socks, where the TUBE and AOTC socks were over-the-calf socks and the ALC and ANC socks were mid-calf level socks. The results indicate the height of the sock top above the ankle portion of the test form at both its initial and final positions, wherein the sock-drop is the difference between these values. Each sock was agitated in three separate runs, wherein the results were averaged and provided below in Table 6.

TABLE 6

SOCK-DROP OF WHITE SOCKS

Height Above Ankle

| Sock ID | Initial | Final | Sock-Drop |
|---|---|---|---|
| ALC | 8.10 | 7.75 | 0.35 |
| ANC | 7.48 | 6.83 | 0.65 |

TABLE 6-continued

SOCK-DROP OF WHITE SOCKS

| | Height Above Ankle | | |
|---|---|---|---|
| Sock ID | Initial | Final | Sock-Drop |
| TUBE* | 10.64 | 9.66 | 0.98 |
| AOTC* | 10.54 | 9.27 | 1.27 |

*These socks exceeded the maximum height of the test form; therefore, the top was pulled to approximately one inch below the top of the test form at the start of the test.

Example 3

Example 3 sets forth the results of agitating black socks, where the DLLOTC and DNOTC socks were over-the-calf socks and the DLKOTC, DNC and DLC socks were mid-calf level socks. The results indicate the height of the sock top above the ankle portion of the test form at both its initial and final positions, wherein the sock-drop is the difference between these values. Each sock was agitated in three separate runs, wherein the results were averaged and provided below in Table 7.

TABLE 7

SOCK-DROP OF BLACK SOCKS

| | Height Above Ankle | | |
|---|---|---|---|
| Sock ID | Initial | Final | Sock-Drop |
| DLLOTC* | 10.64 | 10.56 | 0.08 |
| DNOTC* | 10.68 | 10.10 | 0.58 |
| DLKOTC | 10.08 | 8.98 | 1.10 |
| DLC | 5.16 | 4.85 | 0.31 |
| DNC | 6.20 | 5.89 | 0.31 |

*These socks exceeded the maximum height of the test form; therefore, the top was pulled to approximately one inch below the top of the test form at the start of the test.

Example 4

Example 4 sets forth the results of agitating athletic socks. The results indicate the height of the sock top above the ankle portion of the test form at both its initial and final positions, wherein the sock-drop is the difference between these values. Each sock was agitated in three separate runs, wherein the results were averaged and provided below in Table 8.

TABLE 8

SOCK-DROP OF ATHLETIC SOCKS

| | Height Above Ankle | | |
|---|---|---|---|
| Sock ID | Initial | Final | Sock-Drop |
| Wht/Pur | 7.01 | 5.76 | 1.25 |
| Wht/Pink* | 7.85 | 4.91 | 2.94 |
| Wht/Wht† | 7.10 | 5.85 | 1.25 |
| Wht/Red* | 7.38 | 4.73 | 2.65 |
| Blk/Blk | 7.73 | 5.35 | 2.38 |
| Blk/Red* | 6.66 | 5.63 | 1.03 |

*All socks in this category buckled during the test.
†These socks were on the verge of buckling.

What is claimed is:

1. A method for evaluating sock-drop comprising the steps of:
   a) loading a sock onto a test form;
   b) agitating the test form having the sock thereon with a reciprocating motion for a predetermined time along a main axis of the test form; and
   c) measuring a sock-drop distance traveled by the sock,
   wherein the test form for measuring sock-drop comprises a conical structure having a first position and a second position, the first position corresponds to an area of a human leg below the ankle and above the foot, and the second position corresponds to an area of a human leg on the calf below the knee.

2. The method according to claim 2, further comprising the steps of a) observing any occurrence of sock buckling; and b) recording the elapsed time from the start of the test until buckling occurred.

3. A sock testing apparatus, comprising:
   a) a means for agitation, wherein the means for agitation provides a reciprocating motion; and
   b) a test form removably attached to said means of agitation,
   wherein the reciprocating motion is along a main axis of the test form, and the reciprocating motion has a higher peak deceleration at a first end of the motion than at a second end of the motion.

4. The apparatus according to claim 3, wherein the reciprocating motion is a sinusoid.

5. The apparatus according to claim 3, wherein the test form has dimensions representative of a human leg from a position on the leg from the top of the foot to about the knee.

6. The apparatus according to claim 3, wherein the means for agitation has a peak deceleration in the range of about 30 to about 60 times the force of gravity.

\* \* \* \* \*